United States Patent
Chattopadhyay et al.

(10) Patent No.: US 7,595,348 B2
(45) Date of Patent: Sep. 29, 2009

(54) BUTYL LACTATE EMULSIONS FOR THE PRECIPITATION OF WATER-INSOLUBLE DRUG NANOPARTICLES

(75) Inventors: Pratibhash Chattopadhyay, North Royalton, OH (US); Boris Y. Shekunov, Aurora, OH (US); Adam K. Gibson, Fairlawn, OH (US)

(73) Assignee: Ferro Corporation, Waukegan, IL (US)

( * ) Notice: Subject to any disclaimer, the term of this patent is extended or adjusted under 35 U.S.C. 154(b) by 478 days.

(21) Appl. No.: 11/420,035

(22) Filed: May 24, 2006

(65) Prior Publication Data

US 2007/0275072 A1  Nov. 29, 2007

(51) Int. Cl.
*C09K 3/00* (2006.01)
(52) U.S. Cl. .................. 516/53; 516/20; 514/169; 427/213.3; 424/489; 424/520
(58) Field of Classification Search .......... 424/489, 424/1.25, 1.29, 1.65; 516/53
See application file for complete search history.

(56) References Cited

U.S. PATENT DOCUMENTS

| | | | |
|---|---|---|---|
| 6,790,460 B2 * | 9/2004 | Shefer et al. .......... | 424/489 |
| 6,966,990 B2 | 11/2005 | Chattopadhyay et al. | |
| 6,998,051 B2 | 2/2006 | Chattopadhyay et al. | |
| 7,083,748 B2 | 8/2006 | Chattopadhyay et al. | |
| 2002/0155080 A1* | 10/2002 | Glenn et al. ............... | 424/70.5 |
| 2005/0032900 A1* | 2/2005 | Krauser ............... | 514/570 |
| 2006/0008531 A1 | 1/2006 | Shekunov et al. | |
| 2006/0153921 A1 | 7/2006 | Chattopadhyay et al. | |

OTHER PUBLICATIONS

Comelles et al., "Butyl Lactate: A Useful Cosurfactant To Prepare O/W Microemulsions With SDS," J. Dispersion Science And Technology, 20(7), pp. 1777-1788, 1999, twelve pages.

* cited by examiner

*Primary Examiner*—Johann R Richter
*Assistant Examiner*—Danielle Sullivan
(74) *Attorney, Agent, or Firm*—Rankin, Hill & Clark LLP

(57) ABSTRACT

Emulsions for use in precipitating water-insoluble drug nanoparticles. The continuous phase of the emulsions include water and an external surfactant. The discontinuous phase of the emulsions include butyl lactate, a co-solvent, an internal surfactant and a water-insoluble drug that is solubilized in the discontinuous phase. The emulsions allow for the precipitation of nanoparticles of water-insoluble drugs that are otherwise difficult or impossible to precipitate using conventional emulsion techniques.

3 Claims, 1 Drawing Sheet

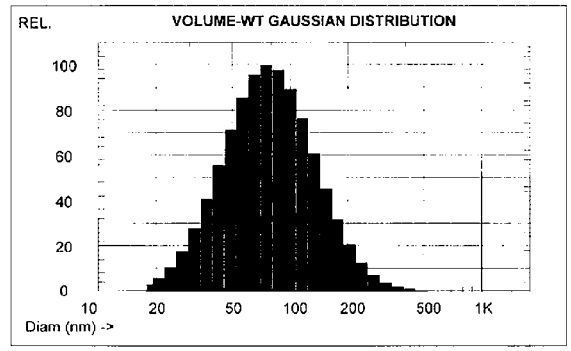

FIG. 1

VOLUME-Weighted GAUSSIAN DISTRIBUTION Analysis (Solid Particle)

GAUSSIAN SUMMARY:

| | | | |
|---|---|---|---|
| Mean Diameter | = 89.8 nm | Chi Squared | = 132.232 |
| Stnd. Deviation | = 49.7 nm (55.4 %) | Baseline Adj. | = 0.016 % |
| Coeff. of Var'n | = 0.554 | Mean Diff. Coeff. | = 5.18E-008 cm2/s |

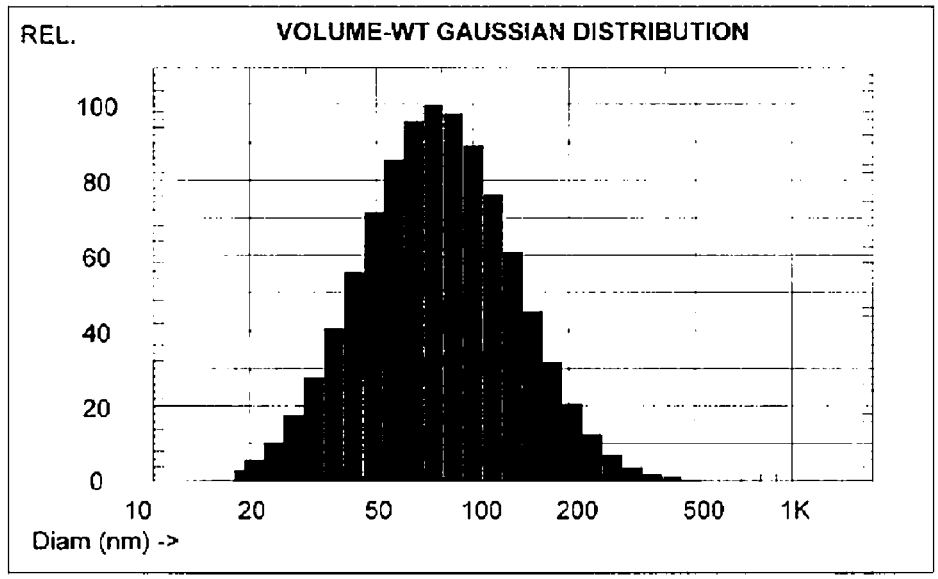

TC189720.184

*Cumulative Result:*
- 25 % of distribution < 49.7 nm
- 50 % of distribution < 71.9 nm
- 75 % of distribution < 104.5 nm
- 90 % of distribution < 146.4 nm
- 99 % of distribution < 260.1 nm

| | | | |
|---|---|---|---|
| Run Time | = 0 Hr 15 Min 25 Sec | Wavelength | = 632.8 nm |
| Count Rate | = 904 KHz | Temperature | = 23 deg C |
| Channel #1 | = 11300.5 K | Viscosity | = 0.933 cp |
| Channel Width | = 21.0 uSec | Index of Ref. | = 1.333 |

BUTYL LACTATE EMULSIONS FOR THE PRECIPITATION OF WATER-INSOLUBLE DRUG NANOPARTICLES

FIELD OF THE INVENTION

The present invention relates to butyl lactate emulsions for the precipitation of water-insoluble drug nanoparticles.

BACKGROUND OF THE INVENTION

Reducing the particle size of a water-insoluble drug often increases the drug's bioavailability. Milling techniques, such as jet milling, ball milling and wet grinding, can be used to reduce the particle size of some drugs, but these techniques cannot be used in some situations due to the possibility of contaminating the drug with grinding media residue or the possibility of degrading the drug due to high shear forces.

Emulsion-based precipitation techniques have been proposed as an alternative means to reduce the particle size of water-insoluble drugs. In these techniques, the water-insoluble drug is dissolved in an organic solvent to form a solution, which is then emulsified in water to become the discontinuous organic ("oil") phase of an oil-in-water ("o/w") emulsion. Small particles can be obtained by removing the organic solvent from the organic phase of the emulsion via evaporation, solvent diffusion and/or by supercritical fluid extraction.

Two factors that are known to significantly affect the particle size and distribution of particles produced using emulsion-based techniques are: (1) the size and uniformity of the oil phase emulsion droplets; and (2) the stability of the emulsion. The particle size and size distribution of the particles produced is directly proportional to the size of the emulsion droplets. Furthermore, it is very difficult to obtain small particles in a narrow size distribution when the emulsion is not sufficiently stable during processing. Some water-insoluble drugs are difficult to incorporate into emulsions, and the presence of such water-insoluble drugs in the oil phase of the emulsion tends to render the emulsion unstable, which leads to emulsion droplet coalescence and/or phase separation and thus poor particle size uniformity upon precipitation.

SUMMARY OF THE INVENTION

Emulsions for use in precipitating water-insoluble drug nanoparticles. The continuous phase of the emulsions include water and an external surfactant. The discontinuous phase of the emulsions include butyl lactate, a co-solvent, an internal surfactant and a water-insoluble drug that is solubilized in the discontinuous phase. The emulsions allow for the precipitation of nanoparticles of water-insoluble drugs that are otherwise difficult or impossible to precipitate using conventional emulsion techniques.

The foregoing and other features of the invention are hereinafter more fully described and particularly pointed out in the claims, the following description setting forth in detail certain illustrative embodiments of the invention, these being indicative, however, of but a few of the various ways in which the principles of the present invention may be employed.

BRIEF DESCRIPTION OF THE DRAWINGS

FIG. 1 is a scanning electron micrograph of nanoparticles formed in the Examples.

DETAILED DESCRIPTION OF THE PREFERRED EMBODIMENTS

The present invention provides emulsions for use in precipitating water-insoluble drug nanoparticles. The emulsions according to the invention comprise a continuous phase and a discontinuous phase. The continuous phase is an aqueous phase that comprises water and an "external" surfactant. The discontinuous phase is an organic phase that comprises butyl lactate, a co-solvent, an "internal" surfactant and a solubilized water-insoluble drug. Throughout the instant specification and in the appended claims, the term "external" when used with reference to the surfactant refers to the surfactant that is present with the water before the emulsion is formed, and the term "internal" when used with reference to the surfactant refers to the surfactant that is present with the butyl lactate/co-solvent before the emulsion is formed.

Emulsions according to the invention can comprise from about 5% to 50% by weight of the discontinuous phase (which is also sometimes referred to as the "organic" or "oil" phase). More preferably, emulsions according to the invention can comprise from about 10 to about 30% by weight of the discontinuous phase, with the balance being the continuous phase (which is sometimes referred to as the "aqueous" or "water" phase).

The discontinuous phase of the emulsion comprises a water-insoluble drug in an amount up to about 50% by weight of the discontinuous phase. The preferred concentration of the water-insoluble drug in the discontinuous phase is from about 2% to about 10% by weight of the discontinuous phase. Virtually any water-insoluble drugs that can be solubilized in butyl lactate, a co-solvent and an internal surfactant can be processed into nanoparticles in accordance with the invention. Examples of suitable water-insoluble drugs include budesonide, carbamazepine, megestrol acetate, dicumerol, metolazone, prazosin HCl, quinestrol, danazol, griseofulvin, prednisilone, prednisone, indomethacin, ketoprofen, acetaminophen, ibuprofen, dexamethasone, itraconazole and cortisone acetate.

As noted, the discontinuous solvent comprises butyl lactate. Butyl lactate can exist in two chemical forms (isomers), namely butyl D-lactate and butyl L-lactate. Generally speaking, butyl lactate is available commercially as a mixture of the two isomers. Butyl lactate is not believed to present toxicity issues when ingested and thus is an excellent solvent for the preparation of drugs and other ingestible materials.

As noted, the discontinuous phase of the emulsion further comprises a co-solvent, which aids in the solubilization of the water-insoluble drug and/or the internal surfactant. Suitable co-solvents for use in the invention include C6 to C10 straight-chain alkanes, dichloromethane, chloroform, and C1 to C4 linear alcohols (e.g., ethanol). Preferred co-solvents include ethanol, hexane and dichloromethane. The amount of co-solvent used will be determined based on the solubility of the water-insoluble drug in butyl-lactate and the amount of internal surfactant used in the discontinuous phase. Preferably, the co-solvent comprises from about 10% to about 30% by weight of the discontinuous phase.

The internal surfactant is preferably lecithin, which may further include varying phosphatydyl choline, phosphatydyl ethanolamine, phosphatydic acid and triglyceride concentrations. The weight ration of internal surfactant to drug in the discontinuous phase is preferable from about 1:1 to about 10:1, and more preferably from about 1:1 to about 4:1. Those having skill in the art will readily recognize that the amount of internal surfactant present in the emulsions according to the invention is substantially lower than the amount typically present in conventional emulsions.

The continuous phase of the emulsion comprises an external surfactant in an amount not greater than about 50% by weight of the continuous phase. The preferred external surfactant concentration is from about 1% to about 5% by weight of the continuous phase.

Suitable external surfactants for use in the invention include, for example, POLYSORBATE-80 (polyethylene sorbitan monooleate, which is available from a variety of suppliers), PLURONIC (block copolymers based on ethylene oxide and propylene oxide available from BASF Corporation), poly vinyl alcohol ("PVA"), poly ethylene glycol, tyloxipol and tocopherol acetate. The presently most preferred external surfactants are POLYSORBATE-80 and PVA.

Emulsions according to the invention are formed by emulsifying an organic solution into an aqueous solution. The aqueous solution can be formed by dissolving the external surfactant in water. The organic solution can be formed by blending the butyl lactate, co-solvent, internal surfactant and water-insoluble drug together. The order of addition is not per se critical, but it is important that the water-insoluble drug be fully solubilizied in the organic solution. Heat and stirring can be used to assist in the solubilization of the water-insoluble drug in the organic solution to the extent that it does not degrade the drug.

Once the aqueous solution and the organic solutions have been prepared, they are contacted together and emulsified. Formation of the emulsions can be accomplished by a variety of methods such as shaking, mechanical or magnetic stirring, or exposure to an ultrasonic field. Emulsions can be preferably prepared using a high-pressure homogenization such that the emulsion droplet size is approximately equivalent to the desired particle size. Alternatively the emulsions can be prepared using a high shear mixer, sonication or by using a colloidal mill. Emulsions according to the invention are preferably processed until a substantially uniform droplet size distribution is obtained, which aids in obtaining water-insoluble drug nanoparticles having a narrow distribution in the desired particle size range.

Emulsions according to the invention are very stable, and can be processed to produce nanoparticles of the water-insoluble drug using conventional emulsion processing techniques. Extraction of the emulsion's discontinuous phase butyl lactate and co-solvent can be accomplished by extraction with supercritical $CO_2$, another supercritical fluid, an organic solvent, membrane permeation, solvent evaporation, or emulsion dilution. The preferred method is extraction with supercritical $CO_2$. Extraction with $CO_2$ is faster and yields a more concentrated aqueous suspension of water-insoluble drug nanoparticles as compared to conventional solvent evaporation or dilution techniques.

The following examples are intended only to illustrate the invention and should not be construed as imposing limitations upon the claims.

EXAMPLE 1

Preparation of Emulsion 0.225 grams of lecithin (ALCOLAC) was dissolved 3.25 grams of butyl lactate and 0.75 grams of hexane co-solvent in a vial. 0.16 grams of budesonide was dissolved in the lecithin/butyl lactate/hexane mixture to form a 4% (w/w) organic budesonide solution.

In a separate 20 ml vial, 0.093 grams of TWEEN-80 was dissolved in 9.3 grams of water. The organic budesonide solution was emulsified into the water using a high-pressure homogenizer (Microfludics Inc.) in 3 passes at 16,000 psi. The emulsion was stable, and no phase separation as observed using an optical microscope in 24 hours. The discontinuous "oil" phase emulsion droplets were substantially uniform and had a size of about 0.5-1.0 microns as observed under the optical microscope.

EXAMPLE 2

Precipitation of Nanoparticles 10 grams of the emulsion formed in Example 1 was loaded into an extraction column (3 feet long) having a volume of 400 ml. It was not necessary to fill the extraction column with any packing material. Supercritical $CO_2$ was then bubbled through the extraction chamber through a 0.5 micron stainless steel frit at the bottom of the extraction chamber. The extraction chamber was maintained at a constant pressure and temperature of 80 bar and 50° C., respectively. The flow rate of the $CO_2$ and the emulsion through the extraction chamber was maintained at a constant rate of 40 ml/min and 0.5 ml/min, respectively. The extraction process was carried out in a continuous fashion. An aqueous colloidal suspension of budesonide nanoparticles was obtained in a continuous fashion from the bottom of the extraction column.

EXAMPLE 3

Analysis of Nanoparticles

Analysis of the aqueous colloidal suspension of nanoparticles obtained from Example 2 was performed using a dynamic light scattering (DLS) instrument. FIG. 1 shows the particle size distribution of the budesonide nanoparticles. The mean volume diameter of the particles based on the DLS measurements was 200-500 nm.

Additional advantages and modifications will readily occur to those skilled in the art. Therefore, the invention in its broader aspects is not limited to the specific details and illustrative examples shown and described herein. Accordingly, various modifications may be made without departing from the spirit or scope of the general inventive concept as defined by the appended claims and their equivalents.

What is claimed is:

1. An emulsion for use in precipitating water-insoluble drug nanoparticles, the emulsion comprising:
   from about 50% to about 95% by weight of a continuous phase comprising:
   water; and
   an external surfactant in an amount not greater than about 50% by weight of the continuous phase; and from about 5% to about 50% by weight of a discontinuous phase comprising:
butyl lactate;
an internal surfactant;
a water-insoluble drug in an amount not greater than about 50% by weight of the discontinuous phase, wherein the water-insoluble drug is solubilized in the discontinuous phase, and wherein the weight ratio of the internal surfactant to the water-insoluble drug is from about 1:1 to about 10:1; and
a co-solvent selected from the group consisting of C6 to C10 straight-chain alkanes, dichloromethane, chloroform and $C_1$-$C_4$ linear alcohols, said co-solvent being present in an amount sufficient to solubilize the water-insoluble drug and/or the internal surfactant in the butyl lactate and thereby form an organic solution that forms the entire discontinuous phase of the emulsion.

2. An emulsion for use in precipitating water-insoluble drug nanoparticles, the emulsion comprising:
from about 70% to about 90% by weight of a continuous phase comprising:
water; and
from about 1 to about 5% by weight of the continuous phase of an external surfactant selected from the group consisting of polysorbate-80, pluronic, poly vinyl alcohol (PVA), poly ethylene glycol and tocopherol acetate; and
from about 10% to about 30% by weight of a discontinuous phase comprising:
butyl lactate;
an internal surfactant;
from about 2% to about 10% by weight of the discontinuous phase of a water-insoluble drug that is solubilized in the discontinuous phase, and wherein the weight ratio of the internal surfactant to the water-insoluble drug is from about 1:1 to about 4:1; and
a co-solvent selected from the group consisting of hexane and dichloromethane, said co-solvent being present in an amount sufficient to solubilize the water-insoluble drug and/or the internal surfactant in the butyl lactate and thereby form an organic solution that forms the entire discontinuous phase of the emulsion.

3. A method of producing nanoparticles of a water-insoluble drug, the method comprising:
providing an emulsion comprising:
from about 50% to about 95% by weight of a continuous phase comprising:
water; and
an external surfactant in an amount not greater than about 50% by weight of the continuous phase; and
from about 5% to about 50% by weight of a discontinuous phase comprising:
butyl lactate;
an internal surfactant;
a water-insoluble drug in an amount not greater than about 50% by weight of the discontinuous phase, wherein the water-insoluble drug is solubilized in the discontinuous phase, and wherein the weight ratio of the internal surfactant to the water-insoluble drug is from about 1:1 to about 10:1; and
a co-solvent selected from the group consisting of C6 to C10 straight-chain alkanes, dichloromethane, chloroform and $C_1$-$C_4$ linear alcohols, said co-solvent being present in an amount sufficient to solubilize the water-insoluble drug and/or the internal surfactant in the butyl lactate and thereby form an organic solution that forms the entire discontinuous phase of the emulsion; and
extracting at least the butyl lactate and the co-solvent from the discontinuous phase of the emulsion using a supercritical fluid to precipitate nanoparticles of the water-insoluble drug and thereby form an aqueous suspension of water-insoluble drug nanoparticles.

* * * * *